United States Patent [19]

Munro et al.

[11] Patent Number: 4,731,366
[45] Date of Patent: Mar. 15, 1988

[54] DISCORHABDIN COMPOSITIONS AND THEIR METHODS OF USE

[75] Inventors: Murray H. G. Munro; Nigel B. Perry; John W. Blunt, all of Christchurch, New Zealand

[73] Assignee: Harbor Branch Oceanographic Institution, Inc., Ft. Pierce, Fla.

[21] Appl. No.: 893,409

[22] Filed: Aug. 5, 1986

[51] Int. Cl.$^4$ ............... C07D 513/22; C07D 471/20; A61K 31/38; A61K 31/395
[52] U.S. Cl. .................................... 514/278; 546/18
[58] Field of Search ......................... 546/18; 514/278

[56] References Cited

U.S. PATENT DOCUMENTS 4,166,174  8/1979  Tanaka et al. .................. 546/18

Primary Examiner—Robert T. Bond
Attorney, Agent, or Firm—Carroll F. Palmer

[57] ABSTRACT

This invention relates to novel discorhabdin compositions which are useful as antitumor, antibacterial and antifungal compositions, a process of producing the compositions and a method for inhibiting tumors, bacteria and fungi utilizing the compositions. More particularly, the novel discorhabdin compositions are organic compounds which are derived from marine sponges genus Latrunculia.

20 Claims, No Drawings

DISCORHABDIN COMPOSITIONS AND THEIR METHODS OF USE

FIELD OF THE INVENTION

This invention relates to new discorhabdin compounds. These compounds have useful antitumor, antibacterial and antifungal activity. Additionally and particularly, this invention relates to new antitumor, antibacterial and antifungal discorhabdin compositions derived from marine organisms, i.e., sponges of the genus Latrunculia, and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well know, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors further antitumor methods and chemical compositions are needed.

Bacteria are of practical importance to man. While some bacteria are useful in industry and for soil firtilization, others are harmful. Bacteria are responsible for diseases in man, other animals and plants including, for example in man, botulism, diphtheria, tetanus and tuberculosis. Bacteria also cause large economic damage due to spoiling of various food, e.g., milk products.

Vast resources and energy have been devoted to bacteriology and immunology relating to bacteria caused diseases. While many methods and chemical compositions have been utilized in controlling bacteria caused disease and other maladies, new antibacterial methods and chemical compositions are needed.

Prevention of the growth of fungus and prevention of the infections and maladies caused to mammals and plants is also of importance to man. The presence of fungus may cause various diseases and infections in man including mycotic disease, e.g., pulmonary candidiasis and pulmonary blastomycosis. Certain yeastlike organisms, e.g., *Cryptococcus neoformans,* may cause serious infections of the central nervous system. More commonly known fungal infections in humans and mammals include ringworm, which are fungus infections of hair and nail areas, as well as resistant infections of the skin. Many other fungal infections inflict humans and mammals in the areas of skin, mucous membranes, intestinal tract, vaginal area and lungs.

Plants are also attacked by various fungi. Damage caused by fungus infection to agriculture amounts to billions of dollars annually. Various inorganic and organic fungistats and fungicides have been tried but with limited success. It is of course important for the fungistat or fungicide to kill the fungi but not the plant and to leave no toxic residue on the food of the plant. Various methods have been utilized to combat fungus infection in agriculture including foliage fungicide by which method plants are coated with a preventive weather-resistant fungicide. Seed treatment and soil treatment are methods which requires fungicides which are safe for seeds and resist degradation by soil and soil microorganisms. Chemotherapeutants are fungicides which permeate the plant to protect new growth or eliminate infections which have already occurred within the plant. Agricultural fungistats and fungicides and their application must also meet very stringent requirements and regulations, which have been promulgated, for example, in the United States.

Considerable research and resources have been devoted to combating fungal infections in both mammals and plants. While some antifungal agents and methods have been developed which aid in inhibiting the spread of fungus and fungus-caused diseases in both mammals and plants and in treating infected mammals and plants new methods and antifungal chemical compositions are needed.

It has now been found that certain organic compounds derived from extracts of sponges of the genus, Latrunculia, posses useful antitumor, antibacterial and antifungal activity. The genus Latrunculia is in the family Latrunculiidae Topsent, order Hadromerida. Twenty-nine species one with three subspecies) of Latrunculia have been described. The genus occurs in cold, temperate and warm seas (Arctic, Antarctic, Kerguelen, New Zealand, Rio de la Plata, Azores, Mediterranean and Red Sea) at depths from less than 20 meters to over 1200 meters.

Some compounds have been previously isolated from marine sponge *Latrunculia magnifica*. These compounds named Latrunculins A, B, C and D are 2—thiazolidinone macrolides and have been reported by Kashman et al, in "Latrunculin; A New 2—Thiazolidine Macrolide", Tetrahedron Letters, 21 page 3629 (1980) and "Latrunculins NMR Study, Two New Toxins and a Synthetic Approach," Tetrahedron 41, 1905-1914, (1985) and references cited therein. The entire disclosure of these references are hereby incorporated herein by reference. The latrunculins are reported to represent a new class of highly potent compounds that disrupt microfilament organization in cultured cells. Thus, marine sponges and other marine life can be a source of useful raw materials for man.

SUMMARY OF THE INVENTION

It is therefore an object of the invention to provide novel compositions which are useful as antitumor, antibacterial and antifungal agents and a process for producing such novel compositions.

It is an additional object of the invention to provide a method for inhibiting tumors, bacteria and fungus growth and resultant infection and disease utilizing novel antitumor, antibacterial and antifungal compositions.

Additional objects and advantages of the invention will be set forth, in part, in the description which follows and in part will be obvious from this description, or may be learned by the practice of the invention. The objects and advantages of the invention are realized and obtained by means of the compositions, process, methods, and the combinations particularly pointed out in the appended claims.

To achieve the objects in accordance with the purposes of the invention, as embodied and fully described here, the invention comprises compositions of the general formulae I-III:

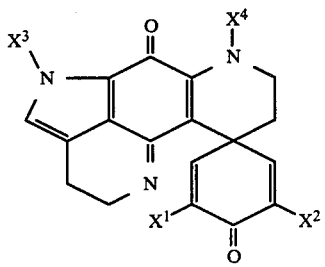

I

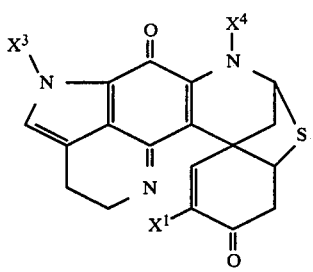

II

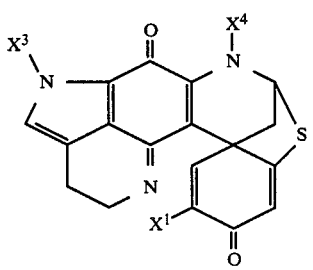

III wherein $X^1$, $X^2$, $X^3$ and $X^4$ are the same or different and are a halogen, hydrogen or hydroxy.

In preferred embodiments of the invention, the composition is substantially pure and $X^1$ or $X^2$, is bromine and $X^3$ or $X^4$ is hydrogen. In more preferred embodiments of the invention, the invention comprises compositions of the formulae IV-VI:

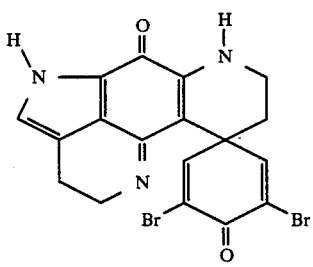

IV

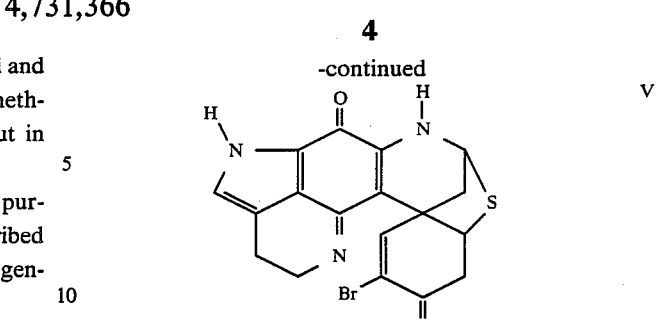

V

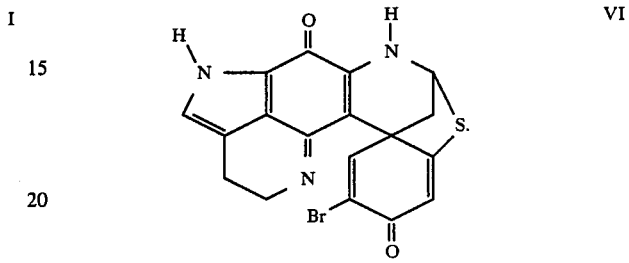

VI

As embodied and fully described herein, the invention also comprises an antitumor, antibacterial or antifungal composition comprising, as active ingredient, an effective an antitumor, antibacterial or antifungal amount of one or more compositions according to formulae I-VI and a non-toxic pharmaceutically acceptable carrier or diluent.

As embodied and fully described herein, the invention also comprises a process to produce the compositions of formulae I-VI. The process comprises the steps of collecting marine sponge of the genus, Latrunculia; contacting the marine sponge with a suitable organic solvent system to obtain an extract; and isolating a composition according to formulae I-VI from the fractionated extract.

As embodied and fully described herein, the invention further comprises a method for inhibiting tumors comprising contacting tumor cells with an effective antitumor amount of one or more compositions of formulae I-VI.

As embodied and fully described herein, the invention further comprises method for inhibiting bacteria comprising contacting bacteria with an effective antibacterial amount of one or more compositions of formulae I-VI.

As embodied and fully described herein, the invention further comprises a method for inhibiting the growth of or killing fungi comprising contacting fungi with an effective antifungal amount of one or more compositions of formulae I-VI.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compositions of the general formulae I–III:

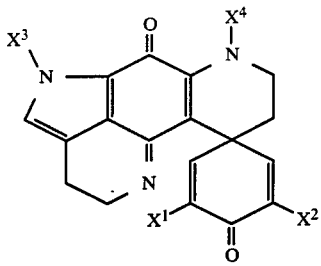

I

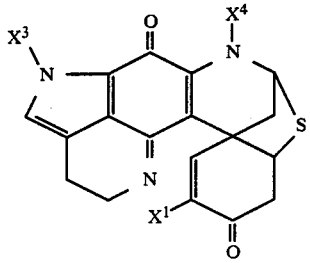

II

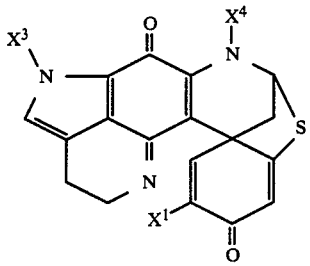

III wherein $X^1$, $X^2$, $X^3$ and $X^4$ are the same or different and are a halogen, hydrogen or hydroxy.

In preferred embodiments of the invention, the composition is substantially pure and $X^1$ or $X^2$ is bromine and $X^3$ and $X^4$ are each hydrogen.

In more preferred embodiments of the invention, the invention comprises compositions of the formulae IV–VI:

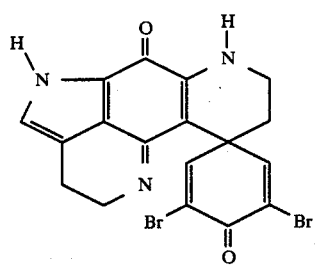

IV

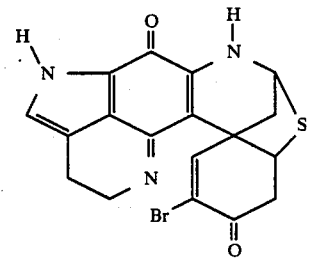

V

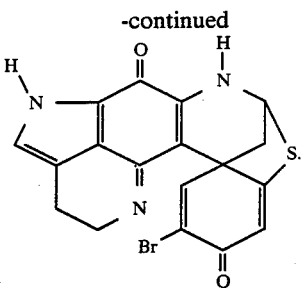

VI

In accordance with the invention, an antitumor composition is provided comprising as active ingredient an effective antitumor amount of one or more of the compositions described above and identified by formulae I–VI in a non-toxic pharmaceutically acceptable carrier or diluent. While effective amounts may vary, as conditions in which the antitumor compositions are used vary, a minimal dosage required for activity is generally between 0.05 and 100 micrograms against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an effective antitumor amount of one or more compositions according to formulae I–VI. The effectiveness of the compositions of the invention for inhibiting tumors indicates their usefulness for controlling tumors in hosts including mammals and for treating cancerous cachexia.

In accordance with the invention, an antibacterial composition is provided comprising as active ingredient an effective antibacterial amount of one or more of the compositions described above and identified by formulae I–VI and a non-toxic pharmaceutically acceptable carrier or diluent. While effective amounts may vary, as conditions in which the antibacterial compositions are used vary, a minimal dosage required for activity is generally less than 40 micrograms against *Escherichia coli* and *Bacillus subtilis* bacteria showing a zone of inhibition of at least 14 mm. Useful examples of non-toxic pharmaceutically acceptable carriers or diluents include, but are not limited to, the following: ethanol, dimethyl sulfoxide and glycerol.

In accordance with the invention, a method for inhibiting bacteria in a host is provided comprising contacting bacteria with an antibacterial amount of one or more compositions according to formulae I–VI. The effectiveness of the compositions of the invention for inhibiting bacteria indicates their usefulness for controlling bacteria and bacterial related diseases in hosts including mammals. Further, such compositions may be utilized to prevent or retard spoilage of food due to the presence and growth of bacteria.

In accordance with the invention, an antifungal composition is provided comprising as active ingredient an effective antifungal amount of one or more of the compositions described above and identified by formulae I–VI in a non-toxic pharmaceutically acceptable carrier or diluent. While effective amounts may vary, as conditions in which the antifungal compositions are used vary, a minimal dosage required for activity is generally between 1 and 10 micrograms/ml against $10^3$ml fungi such as, *Candida albicans*, for example. Useful examples of non-toxic pharmaceutically acceptable carriers or diluents include, but are not limited to, the following: ethanol, dimethyl sulfoxide and glycerol.

In accordance with the invention, a method for inhibiting fungus in a host is provided comprising contacting fungus with an antifungal amount of one or more compositions according to formulae I–VI. The effectiveness of the compositions of the invention for inhibiting fungus indicates their usefulness for controlling fungus and fungus related diseases in hosts including mammals. Further, such compositions may be useful as agricultural fungicides.

In accordance with the invention, a process is provided to produce the compositions of formulae I–VI. The process comprises the steps of collecting samples of marine sponge of the genus, Latrunculia; contacting the marine sponge with a suitable organic solvent system to obtain an extract; partitioning said extract by reverse phase chromatography to obtain a number of fractions; and isolating a composition according to formulae I–VI from the fractionated extract.

In preferred embodiments of the invention the suitable organic solvent system is selected from the group of solvents consisting of methanol, toluene, methylene chloride, acetone, methyl ethyl ketone, ethyl acetate, ethanol, methyl isobutyl ketone and mixtures thereof. Particularly preferred solvent systems are mixtures of methanol with either toluene or methylene chloride.

While those solvents listed above are the presently preferred choices for the solvents useful in accordance with the invention, other suitable solvents may be substituted. A suitable solvent system should be capable of extracting a compound according to any one of formula I–VI from other components of the sponge. Different ratios of solvents and any combination may be used in the solvent system of the invention as would be known to those skilled in the art.

Compositions according to the invention are synthesizing and/or isolating by various synthetic and chromatographic techniques from the fractions obtained. Any suitable fractionation and isolation techniques as known to those skilled in the art may be utilized in accordance with the process of the invention. Suitable fractionation techniques include various chromatography techniques such as, reverse phase flash chromatography (RPFC) or reverse phase liquid chromatography (RPLC) with suitable columns as would be known to those skilled in the art (e.g., an Alltech C8 column or Merck Lobar LiChroprep RP-8 (column) eluted with a suitable solvent such as, for example 4:1 to 1:4, methanol: $H_2O + 0.05\%$ trifluoroacetic acid).

A more detailed description and explanation of a preferred embodiment of the process of the invention to produce a compound according to formulae I–VI is provided in the examples section.

It is therefore apparent that the compositions of the invention, the process for producing the compositions of the invention and the methods for utilizing the compositions of the invention are effective for inhibiting or destroying tumors, bacteria and fungus and therefore controlling diseases, infections and spoilage caused by or related to such tumors, bacteria and fungus in fulfillment of the objects of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose methods of preparation are not indicated are commercially available from sources known to the art such as chemical supply houses.

EXAMPLE 1

Preparation of Discorhabdin C:

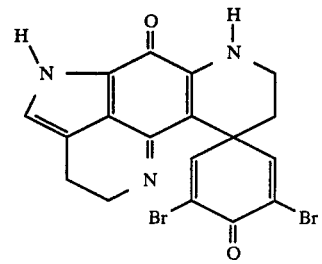

Red-brown marine sponge of the genus Latrunculia du Bocage, were collected by trawling and SCUBA diving at depths of 20 to 75 meters off of the Kaikoura Peninsula, New Zealand. 150 gms. of the sponge was cut into pieces, freeze-dried, ground to a powder and extracted by percolating with methanol/toluene (3:1, 1L). Removal of the solvents gave a brown paste (9.7 g) which was coated onto reverse-phase (RP) material (Merck LiChroprep RP-8, 40–63 μm, ca. 10 gms.) and introduced, as an aqueous slurry, to the top of a chromatographic column packed with the same material (ca. 40 gms.).

Elution with water followed by a steep, stepped gradient through methanol to dichloromethane gave 12 fractions. The cytotoxic fractions 5 to 9 were combined (0.77 gms.) coated onto RP material (6gms.), and loaded into a precolumn. This was connected to a preparative RP column (Merck Lobar LiChroprep RP-8, 25 mm×250 mm) and eluted with 40% MeOH, 60% $H_2O + 0.05\%$ trifluoroacetic acid (TFA)) at 9 ml/min. Fractions containing the major component were combined and evaporated (0.28 gms.). A subsample (20 mg) of this material was further purified by semi-preparative RPLC (Alltech C8 column, 250 mm×10 mm), eluting with 70% MeOH 30% $H_2O + 0.05\%$ TFA, at 5 ml/min.

This gave discorhabdin C (12 mg) which was characterized as its hydrochloride salt, a red solid soluble in MeOH, $H_2O$ and dimethylsulfoxide (DMSO): mp.>360°; $[\alpha]_D 0°$ (c 0.05, MeOH); IR(KBr) 3700–2500, 1675, 1585, 1540, 1325, 1020, 695 cm$^-$; UV(MeOH) 245 ($\epsilon$28500), 351 ($\epsilon$10000), 545 nm ($\epsilon$500); UV(MeOH/KOH) 337 ($\epsilon$13000), 481 nm ($\epsilon$1500); $^1$H NMR (d$_4$-MeOH, 80 MHz)$\delta$7.70 (s, 2H), 7.28 (s, 1H), 4.0-3.7 (m, 4H), 3.0 (t, J=8 Hz, 2H), 2.2 ppm (t,J=6 Hz,2H); $^{13}$C NMR $\delta$171.5 (s), 165.5 (s), 153.3 (s), 151.9 (s), 151.4 (2×d), 127.8 (d), 123.7 (s), 123.3 (s), 122.7 (2×s), 120.0 (s), 91.8 (s), 44.8 (s), 43.8 (t), 38 (t), 33.8 (t), 18.2 (t), FABMS (glycerol matrix) m/z 462/464/466 (MH+).

EXAMPLE 2

Preparation of Discorhabdin A:

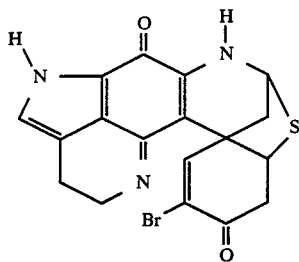

Green marine sponges of the genus Latrunculia du Bocage, were collected by trawling and scuba diving at depths of from 110 to 145 meters off of the Kailkoura Peninsula, New Zealand, in December 1982. 168 gms of the green sponge was blended and extracted with MeOH and $CH_2Cl_2$ to give, after removal of solvents, a green extract (11.3 gms). This was partitioned on a reverse phase (RP) column to give a number of cytotoxic fractions containing largely discorhabdin A. Semi-preparative RPLC (Alltech C8 column; 250 mm×10 mm; 5 ml/min 65% MeOH 35% $H_2O$+0.05% trifluoroacetic acid); 210 nm detection gave pure discorhabdin A.

Properties, as hydrochloride: Green solid; mp>360°, soluble in MeOH, $H_2O$, and DMSO; $[\alpha]_D$+400° (c 0.05, MeOH); contains Br, Cl and S by X-ray fluorescence; combustion analysis: C 45.09%, H 3.08%, N 8.51%, Cf-252 MS: 416/418($MH^{30}$);
FABMS: 416/418 ($MH^{D}+$);
EIMS: 383/385 (M-S);
IR (KBr): 3700-2400, 1680, 1620, 1585, 1530, 1410, 1385, 530 $cm^{-1}$;
UV(MeOH) 249 ($\epsilon$29500), 351 ($\epsilon$10500), 567 nm ($\epsilon$900);
UV(MeOH/KOH) 335 ($\epsilon$14000), 473 nm ($\epsilon$1000); $^1H$ NMR (d4-MeOH, 80 MHz)$\delta$7.64 (s, 1H), 7.24 (s, 1H), 5.40 (dd, J=1.0, 3.8 1Hz, 1H), 4.55 (dd, J=6.8, 12.2 Hz, 1H), 3.8–4.1 (m, 2H), 3.2–2.8 (m, 5H), 2.60 ppm (brd, J=12.6 Hz, 1H);
$^{13}C$ NMR (d6-DMSO, 20 MHz)$\delta$7 186.7 (s), 165.8 (s), 153.6 (s), 150.2 (s), 148.0 (d), 127.3 (d), 125.9 (s), 123.3 (2×s), 19.8 (s), 103.8 (s), 58.8 (d), 53.8 (d), 49.6 (s), 44.5 (t), 44.4 (t), 42 (t), 18.1 ppm (t).

EXAMPLE 3

Preparation of Discorhabdin B:

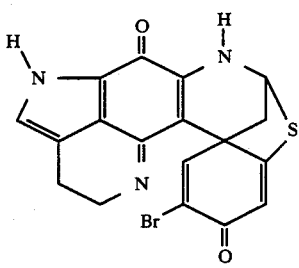

Green marine sponges of the genus Latrunculia du Bocage were collected by trawling and SCUBA diving at depths of 20 to 75 meters off the Kaikoura Peinsula, New Zealand. A sponge sample (178 g) was freeze-dried and ground, then extracted with methanol and toluene to give, after removal of solvents, a green extract (12.7 g). This was partitioned on a reverse phase (RP) column to give a number of cytotoxic fractions containing largely dicorhabdin B. Two further stages of preparative RPLC (Merck LOBAR RP-8 column; 250 mm×25 mm; 4 ml/min 35% MeOH, 65% [$H_2O$+0.05% trifluoroacetic acid]) gave pure dicorhabdin B.

Properties, as a hydrochloride: a green solid which is sparingly soluble in MeOH and $H_2O$, soluble in DMSO; contains Br Cl and S by X-ray fluorescence.
IR (KBr): 3700-2400, 1740, 1650, 1620, 1520, 1410, 530 $cm^{-1}$; $^1H$ NMR (d4-MeOH, 300 MHz)$\delta$7.87 (s, 1H), 7.21 (s, 1H), 6.24 (s, 1H), 5.72 (d, J=4.0 Hz, 1H), 3.72–4.00 (m, 2H), 2.90–2.95 (m, 2H), 2.81 (d, J=11.5 Hz, 1H), 2.54 (dd, J=4.0, 11.5 Hz, 1H); $^{13}C$ NMR (d6-DMSO, 20 MHz)$\delta$173.4 (s), 169.2 (s), 164.5 (s), 153.6 (s), 150.4 (s), 145.4 (d), 127.6 (s), 127.2 (d), 123.0 (s), 122.6 (s), 119.8 (s), 118.8 (d), 96.7 (s), 60.8 (d), 50.7 (s), 44.8 (t), ca 41 (t), 17.6 (t) ppm.

ANTIMICROBIAL AND CYTOTOXICITY ASSAY PROTOCOL

Antimicrobial assays. The discorhabdins A, B, and C were screened against *Escherichia coli*, *Bacillus subtilus*, and *Pseudomonas aeruginosa* using pre-seeded 85 mm petri dishes. Bioassay discs (6 mm) were loaded with fixed aliquots of the test solutions, air dried and applied to the plates. These were incubated at 35° C. for 18 hrs. and the diameters of the inhibition zones recorded.

Cytotoxicity assays. Assay wells were prepared by seeding 15 mm wells with 1 ml of a 3.0×$10^4$ cells/ml suspension of BSC (monkey kidney) cells in Eagle MEM containing 5% calf serum (EM5C). The wells were incubated in a humidified $CO_2$ incubator at 37° until 85–90% confluent. The medium was aseptically aspirated from the wells and overlayed with 1 ml of Eagle MEM containing 2% Nu Serum and 2% 4KCPS methyl cellulose. Bioassay discs (6 mm) were loaded with the desired amount of test solution, air dried and applied to the monolayer by pushing the discs through the overlay and the wells incubated in a 5% $CO_2$ enriched atmosphere at 37° C. for 24 hrs. The zone of cytotoxicity was measured using an inverted microscope. The measure of cytotoxicity was rated on the diameter of the zone as follows:
+: 6–8 mm
++: 8–10 mm
+++: 10–12 mm
++++: 12–15 mm.

ANTITUMOR ACTIVITIES OF THE COMPOUNDS OF THE INVENTION

The following assay method was utilized to illustrate the antitumor effectiveness of the discorhabdin compositions of the invention.

L1210 AND P388 MOUSE LEUKEMIA CELL ASSAY

Maintenance of Cell Line

L1210 and P388 mouse leukemia cells are grown in Dulbecco MEM medium with 10% horse serum, 4 mM glutamine, and 20 μg/ml gentamycin (Biologos, Inc.). Cells are incubated in 10% $CO_2$ and subcultured 2 times per week.

PROCEDURE

1. Add composition to each well of a 24-well plate or tube and allow solvent to evaporate to dryness.
2. Add 2 ml (1.2×$10^5$) cells to each well or tube and mix.

3. Incubate in 10% $CO_2$ at 37° for 48 hours.

4. Read plates with an inverted microscope, scoring activity from 1+ to 4+ as follows: ND (not detectable),>90%; 1+, 75-90%; 2+, 50-74%; 3+, 25-49%; 4+,<25% of control growth. Cell counts are performed on each tube and results are reported as percent of control.

5. Antitumor activity is alternatively expressed as $IC_{50}$ amount which is the minimum concentration necessary to achieve a 50% inhibition growth of tumor cells in the plates.

ANTIFUNGAL ACTIVITIES OF THE COMPOSITIONS OF THE INVENTION

The following assay method was utilized to demonstrate the in vitro antifungal effectiveness of the discorhabdin compositions of the invention as reported in table 1.

Preparation of inocula

Candida albicans: *C. albicans* (CA) is grown on Sabouraud dextrose agar to produce single colonies one of which is used to inoculate Sabouraud dextrose broth. The broth is incubated at 37° C. with shaking at 200 rpm for 18 hrs., the resultant culture is frozen with 10% (v/v) glycerol at −80° C. and used as the inoculum for the anti-Candida assay.

Assay protocols

Disc diffusion assay

*C. albicans* is inoculated into melted Sabouraud dextrose agar at 45° C. to give a cell density of approximately 1000 cells/ml. Plates are prepared with 10 ml of the seeded agar in a 10 cm×10 cm petri dish. These plates are stored at 4° C. until needed for the assay.

Paper discs (6.35 mm) are impregnated with the test substance and allowed to dry. They are then placed onto the surface of a test plate prepared as detailed above. Plates are incubated overnight at 37° C. after which time the zones of growth inhibition can be read, these are expressed as the diameter of the zone in millimeters.

TABLE 1

Formula I/IV Pure discorhabdin C. hydrochloride:
BSC cells, 0.05 µg/ml. ++zone.
L1210 cells, $IC_{50}$ 0.03 µg/ml.
*E. coli.*, 40 µg/disk, 14 mm zone
*B. subtilis* 40 µg/disk, 16 mm zone
*C. albicans*, 40 µg/disk, 9 mm zone
*P aeruginosa*, 40 µg/disk, no effect
Formula II/V Pure discorhabdin A hydrochloride:
BSC cells, 0.05 µg/ml. +++zone
*E. coli*, 40 µg/disk, 17 mm zone
*B. subtilis*, 40 µg/disk, 13 mm zone
*C. albicans*, 40 µg/disk, 11 mm zone
*P. aeruginosa*, 40 µg/disk, no effect
L1210 cells, $IC_{50}$, 0.05 µg/ml
P388 cells, $IC_{50}$ 0.5µg/ml
Formula III/VI Pure discorhabdin B hydrochloride:
*B. subtilis*, 40 µg/disk, 19 mm zone
*E. coli*, 40 µg/disk, 13 mm zone
*C. albicans*, 40 µg/disk, 14 mm zone The above results report that discorhabdins A, B, and C are active antibacterial, antifungal, and antitumor agents in vitro. These results indicate that discorhabdin compositions of formulae I-VI are useful to inhibit bacterial fungus and tumor growth in hosts and to inhibit diseases in hosts caused by such bacteria, fungus and tumors.

The scope of the present invention is not limited by the description, examples, and suggested uses herein and modifications can be made without departing from the spirit of the invention. The discorhabdin compositions of the present invention have a novel molecular skeleton from which many derivative compounds or series of compounds may be prepared. The present invention contemplates such derivatives as modifications of the present invention and within the scope of the invention. For example, it may be noted that other derivatives of the compounds of examples 1 and 2 such as hydroxy or fluorine substituted derivative may be prepared that may possess antitumor, antibacterial or antifungal activity analogous to those preferred embodiments described above. Further, the compositions described herein may have other useful applications such as, for example, analgesic applications or a starting materials for the preparations of other compositions. Therapeutic application of the compositions of the present invention can be accomplished by any suitable therapeutic method and technique as is presently or prospectively known to those skilled in the art. Thus, it is intended that the present invention cover the modifications and variations of this invention provided that they come within the scope of the appended claims and their equivalents.

What is claimed is:

1. A compound according to any one of the formulae:

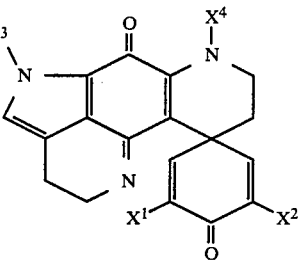

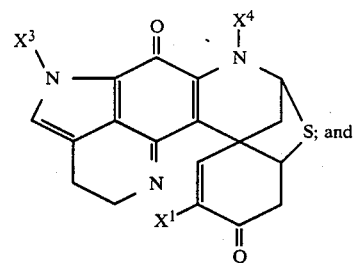

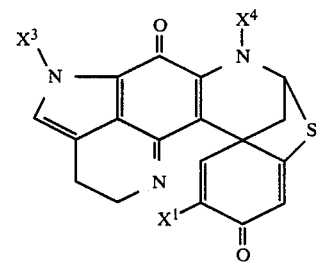

wherein $X^1$, $X^2$, $X^3$ and $X^4$ are the same or different and are a halogen, hydrogen or hydroxy.

2. A compound according to claim 1 wherein at least one of $X^1$ and $X^2$ are Br and $X^3$ and $X^4$ are each hydrogen.

3. A composition according to claim 1 of the formulae:

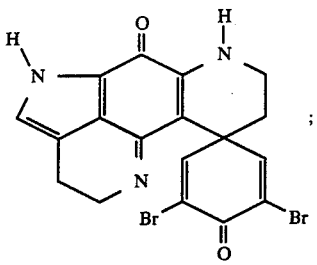

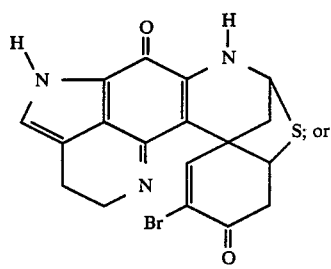

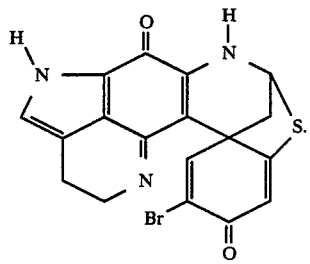

4. The compound according to claim 1 wherein said composition is substantially pure.

5. A compound according to claim 3 wherein said composition is substantially pure.

6. An antitumor composition comprising, as active ingredient, an effective antitumor amount of one or more of the compounds of claim 1 and a non-toxic pharmaceutically acceptable carrier or diluent.

7. A method for inhibiting tumors in a host comprising contacting a tumor with an effective antitumor amount of one or more compounds of claim 1.

8. A method of inhibiting tumors in a host comprising contacting a tumor with an effective antitumor amount of one or more compounds of claim 3.

9. A method for inhibiting tumors in a mammalian host comprising contacting a tumor with an effective antitumor amount of one or more compounds of claim 1.

10. An antibacterial composition comprising, as active ingredient, an effective antibacterial amount of one or more of the compounds of claim 1 and a non-toxic pharmaceutically acceptable carrier or diluent.

11. A method for inhibiting bacteria comprising contacting bacteria with an effective antibacterial amount of one or more compounds of claim 1.

12. A method of inhibiting bacteria in a host comprising contacting bacteria with an effective antibacterial amount of one or more compounds of claim 1.

13. method for inhibiting bacteria in a mammalian host comprising contacting bacteria with an effective antibacterial amount of one or more compounds of claim 1.

14. An antifungal composition comprising, as active ingredient, an effective antifungal amount of one or more of the compounds of claim 1 and a non-toxic pharmaceutically acceptable carrier or diluent.

15. A method for inhibiting fungus growth comprising contacting fungus with an effective antifungal amount of one or more compounds of claim 1.

16. A method of inhibiting fungus growth in a host comprising contacting fungus with an effective antifungal amount of one or more compounds of claim 1.

17. A method for inhibiting fungus growth in a mammalian host comprising contacting fungus with an effective antifungal amount of one or more compounds of claim 1.

18. A process to produce a compound according to claim 1 comprising the steps of:
   collecting marine sponge genus Latrunculia;
   contacting said sponge with a suitable organic solvent system;
   obtaining a solvent extract from the sponge; and
   isolating by chromatographic methods a compound according to claim 1 from the extract.

19. A therapeutic method for treating cancerous cachexia caused by the presence of a tumor in a host comprising contacting cells of said tumor with an effective antitumor amount of a compound according to claim 1.

20. A therapeutic method for treating cancerous cachexia caused by the presence of a tumor in a host comprising contacting cells of said tumor with an effective antitumor amount of a compound according to claim 3.